(12) United States Patent
Solazzi (10) Patent No.: US 9,841,360 B1
(45) Date of Patent: Dec. 12, 2017

(54) SAMPLE CUP ASSEMBLY, SYSTEM AND METHOD FOR PURGING

(71) Applicant: Michael C. Solazzi, Palm City, FL (US)

(72) Inventor: Michael C. Solazzi, Palm City, FL (US)

( * ) Notice: Subject to any disclaimer, the term of this patent is extended or adjusted under 35 U.S.C. 154(b) by 785 days.

(21) Appl. No.: 14/051,555

(22) Filed: Oct. 11, 2013

Related U.S. Application Data

(60) Provisional application No. 61/713,672, filed on Oct. 15, 2012.

(51) Int. Cl.
| | |
|---|---|
| *G01N 1/00* | (2006.01) |
| *G01N 23/22* | (2006.01) |
| *B01L 3/00* | (2006.01) |
| *G01N 23/20* | (2006.01) |
| *G01N 30/40* | (2006.01) |

(52) U.S. Cl.
CPC .................. *G01N 1/00* (2013.01); *B01L 3/50* (2013.01); *B01L 3/508* (2013.01); *B01L 3/5082* (2013.01); *B01L 3/50825* (2013.01); *G01N 23/20025* (2013.01); *G01N 23/2204* (2013.01); *B01L 3/52* (2013.01); *B01L 3/523* (2013.01); *G01N 2001/002* (2013.01); *G01N 2001/005* (2013.01); *G01N 2030/402* (2013.01); *G01N 2201/0233* (2013.01)

(58) Field of Classification Search
CPC ...................................................... G01N 23/10
See application file for complete search history.

(56) References Cited

U.S. PATENT DOCUMENTS

| | | | | |
|---|---|---|---|---|
| 2,127,397 | A | | 3/1938 | Freedlander |
| 2,144,255 | A | | 1/1939 | Carpenter |
| 2,654,250 | A | * | 10/1953 | Harrington ............... G01N 1/12 73/864.61 |
| 3,042,314 | A | * | 7/1962 | Packard ................ B05B 7/2443 239/310 |
| 3,799,723 | A | * | 3/1974 | Lally ....................... B29C 45/28 249/121 |
| 3,881,872 | A | * | 5/1975 | Naono .................... G01N 35/00 134/21 |
| 4,037,109 | A | | 7/1977 | Hosokawa et al. |
| 4,046,138 | A | | 9/1977 | Libman et al. |
| 4,148,732 | A | | 4/1979 | Burrow et al. |
| 4,184,360 | A | | 1/1980 | Vadnay et al. |

(Continued)

FOREIGN PATENT DOCUMENTS

DE          1222425       8/1966

*Primary Examiner* — R. A. Smith
*Assistant Examiner* — Herbert K Roberts
(74) *Attorney, Agent, or Firm* — Keene IP Law, LLC (57) ABSTRACT

A sample analysis cup assembly, system and method for purging including a cell body, including a top end; a bottom end; a cell body wall extending axially from the top end to the bottom end; a transverse wall adjacent the top end, including a plurality of apertures extending therethrough; and a raised portion on the transverse wall including a central aperture extending therethrough; a rotatable cap, including a top surface; a bottom surface; and a series of apertures extending from the top surface through the bottom surface, the rotatable cap being structured to engage with the top end of the cell body; and a ring member structured to couple with the bottom end of the cell body are provided.

11 Claims, 9 Drawing Sheets

(56) References Cited

U.S. PATENT DOCUMENTS

| | | | |
|---|---|---|---|
| 4,256,474 A | 3/1981 | Berger, Jr. et al. | |
| 4,301,010 A | 11/1981 | Eddleman et al. | |
| 4,346,299 A | 8/1982 | Mitteldorf | |
| 4,362,047 A | 12/1982 | vonReis et al. | |
| 4,402,909 A | 9/1983 | Solazzi | |
| 4,409,854 A | 10/1983 | Solazzi | |
| 4,448,311 A | 5/1984 | Houser | |
| 4,575,869 A * | 3/1986 | Torrisi | G01N 23/2204 356/246 |
| 4,587,666 A | 5/1986 | Torrisi | |
| 4,590,792 A * | 5/1986 | Chiang | G01N 1/2208 250/440.11 |
| 4,643,033 A | 2/1987 | Solazzi | |
| 4,665,759 A | 5/1987 | Solazzi | |
| 4,698,210 A * | 10/1987 | Solazzi | G01N 23/2204 250/428 |
| 4,873,876 A * | 10/1989 | Sheridan | G01N 1/10 73/863.73 |
| 4,961,916 A | 10/1990 | Lesage et al. | |
| 4,974,244 A | 11/1990 | Torrisi | |
| 4,982,615 A | 1/1991 | Sultan et al. | |
| 5,323,441 A | 6/1994 | Torrisi et al. | |
| 5,336,324 A * | 8/1994 | Stall | C23C 14/243 118/715 |
| 5,351,281 A | 9/1994 | Torrisi | |
| 5,353,949 A * | 10/1994 | Seibert | B01D 46/0094 220/304 |
| 5,451,375 A | 9/1995 | Solazzi | |
| 5,454,020 A | 9/1995 | Solazzi | |
| RE35,506 E | 5/1997 | Solazzi | |
| 5,630,989 A | 5/1997 | Solazzi | |
| 5,928,935 A * | 7/1999 | Reuss, Jr. | B01L 3/508 215/307 |
| 6,009,766 A | 1/2000 | Solazzi | |
| 6,270,060 B1 * | 8/2001 | Yost | F02M 9/06 261/44.3 |
| 6,428,751 B1 | 8/2002 | Solazzi | |
| 6,519,543 B1 * | 2/2003 | Giannuzzi | G01N 1/32 438/14 |
| 7,261,860 B1 * | 8/2007 | Vellinger | A01K 41/00 119/300 |
| 7,543,723 B2 * | 6/2009 | Wilford | B65D 47/242 137/588 |
| 7,722,821 B2 | 5/2010 | Solazzi | |
| 7,981,380 B2 | 7/2011 | Solazzi | |
| 8,043,862 B2 | 10/2011 | Solazzi | |
| 8,404,197 B2 | 3/2013 | Solazzi | |
| 2002/0008161 A1 * | 1/2002 | Ketcham | B05B 7/2443 239/310 |
| 2002/0066712 A1 * | 6/2002 | Brockwell | B01L 3/50825 215/247 |
| 2002/0186271 A1 * | 12/2002 | Yamada | B41J 2/1652 347/30 |
| 2003/0106492 A1 * | 6/2003 | Levinson | B01J 19/0046 117/200 |
| 2003/0123057 A1 * | 7/2003 | Lemmo | B01J 19/0046 356/301 |
| 2005/0074352 A1 * | 4/2005 | Luo | G03F 1/64 417/572 |
| 2006/0283896 A1 * | 12/2006 | Kasting | B65D 47/24 222/549 |
| 2007/0025881 A1 * | 2/2007 | Thompson | G01N 1/2214 422/513 |
| 2007/0144959 A1 * | 6/2007 | Zuk | B01D 29/085 210/473 |
| 2008/0011360 A1 * | 1/2008 | Bell | G05D 16/10 137/505.11 |
| 2008/0068707 A1 * | 3/2008 | Goodman | B01L 3/0275 359/368 |
| 2008/0113425 A1 * | 5/2008 | Cortelazzo | A61B 10/0096 435/284.1 |
| 2008/0240986 A1 * | 10/2008 | Chang | A61B 10/007 422/68.1 |
| 2010/0106053 A1 * | 4/2010 | Videbaek | A61B 10/0096 600/564 |
| 2010/0151676 A1 * | 6/2010 | Ritchie | C23C 16/34 438/660 |
| 2011/0016950 A1 * | 1/2011 | Ducreux | G01N 1/2214 73/23.42 |
| 2011/0051134 A1 * | 3/2011 | Solazzi | B01L 3/508 356/300 |
| 2011/0207209 A1 * | 8/2011 | Hammons | C12M 23/42 435/297.1 |
| 2011/0247435 A1 * | 10/2011 | Brinker | B01F 7/161 73/864.01 |
| 2012/0183956 A1 * | 7/2012 | Ross | G01N 1/44 435/6.1 |
| 2014/0255984 A1 * | 9/2014 | Sharpin | G01N 1/00 435/38 |
| 2015/0203258 A1 * | 7/2015 | Staton | C12M 23/04 220/371 |

* cited by examiner

SAMPLE CUP ASSEMBLY, SYSTEM AND METHOD FOR PURGING

CROSS-REFERENCE TO RELATED APPLICATION

This application claims the benefit of U.S. Provisional Application No. 61/713,672, filed on Oct. 15, 2012, the entire disclosure of which is hereby incorporated by reference herein.

FIELD OF THE INVENTION

The invention relates generally to sample cups, and more particularly, to sample cups used in spectrochemical analysis.

BACKGROUND OF THE INVENTION

Sample cups are used with spectroscopic instrumentation to determine the characteristics or properties of various substances contained in the cups. The sample substances are disposed in a central chamber of a sample cup for analysis. The sample cup may include a thin film of material disposed across one end of the cup to retain the sample. The sample substance contained in the cup is subjected to analysis when energy beams impinge upon the thin film.

During transportation to the analysis chamber, the thin film of material disposed on a sample cup needs to remain taut and free of wrinkles or creases. Otherwise, the data obtained during analysis may not be precise or accurate. In addition, in preparing for analysis, it may be necessary to purge the sample analysis cup with a gas to remove entrapped air, which can lead to inaccurate results when present.

There remains a need for sample cups with means for introducing a gas into an assembled sample cup, and for permitting the escape of the gas.

SUMMARY OF THE INVENTION

According to an aspect of the invention, a sample analysis cup assembly includes: a cell body, including a top end; a bottom end; a cell body wall extending axially from the top end to the bottom end; a transverse wall adjacent the top end, including a plurality of apertures extending therethrough; and a raised portion on the transverse wall including a central aperture extending therethrough; a rotatable cap, including a top surface; a bottom surface; and a series of apertures extending from the top surface through the bottom surface, the rotatable cap being structured to engage with the top end of the cell body; and a ring member structured to couple with the bottom end of the cell body is provided.

According to an aspect of the invention, a sample cup system includes: a cell body, including a top end; a bottom end; a cell body wall extending axially from the top end to the bottom end; a transverse wall adjacent the top end, including a plurality of apertures extending therethrough; and a raised portion on the transverse wall including a central aperture extending therethrough; a rotatable cap, including a top surface; a bottom surface; and a series of apertures extending from the top surface through the bottom surface, the rotatable cap being structured to engage with the top end of the cell body; a thin film of material; a ring member structured to couple with the bottom end of the cell body and to attach the thin film of material to the cell body; and a stacking adapter structured to engage with the rotatable cap and the ring member upon assembly of a sample cup is also provided.

According to another aspect of the invention, a method for purging a sample analysis cup includes the steps of: providing a cell body, including a top end; a bottom end; a cell body wall extending axially from the top end to the bottom end; a transverse wall adjacent the top end, including a plurality of apertures extending therethrough; and a raised portion on the transverse wall including a central aperture extending therethrough; disposing a rotatable cap onto the cell body, the rotatable cap including a top surface; a bottom surface; and a series of apertures extending from the top surface through the bottom surface, the rotatable cap being structured to engage with the top end of the cell body; providing a ring member structured to couple with the bottom end of the cell body; disposing a thin film of material between the bottom end of the cell body and a ring member, thereby assembling a sample cup; rotating the rotatable cap about the top end of the cell body to selectively align the plurality of apertures of the transverse wall with one or more selected apertures from the series of apertures; and introducing a gas into the central aperture to purge the assembled sample cup, the selectively aligned apertures permitting the escape of the gas is also provided.

BRIEF DESCRIPTION OF THE DRAWINGS

Throughout the drawings, like reference numerals are used to indicate common features of the described devices.

The above-identified drawing figures set forth several of the embodiments of the invention. Other embodiments are also contemplated, as disclosed herein. The disclosure represents the invention, but is not limited thereby, as it should be understood that numerous other modifications and embodiments may be devised by those skilled in the art which fall within the scope and spirit of the invention as claimed.

DETAILED DESCRIPTION OF THE INVENTION

As used herein, the terms "comprises", "comprising", "includes", "including", "has", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "of" refers to an inclusive "or" and not to an exclusive "or". For example, a condition A or B is satisfied by any one of the following: A is true (or present) and B is false (or not present); A is false (or not present) and B is true (or present); and both A and B are true (or present).

The terms "a" or "an" as used herein are to describe elements and components of the invention. This is done for convenience to the reader and to provide a general sense of the invention. The use of these terms in the description herein should be read and understood to include one or at least one. In addition, the singular also includes the plural unless indicated to the contrary. For example, reference to a device containing "a member" includes one or more members. As used in this specification and the appended claims, the term "or" is generally employed in its sense including "and/or" unless the content clearly dictates otherwise.

Figure 1:
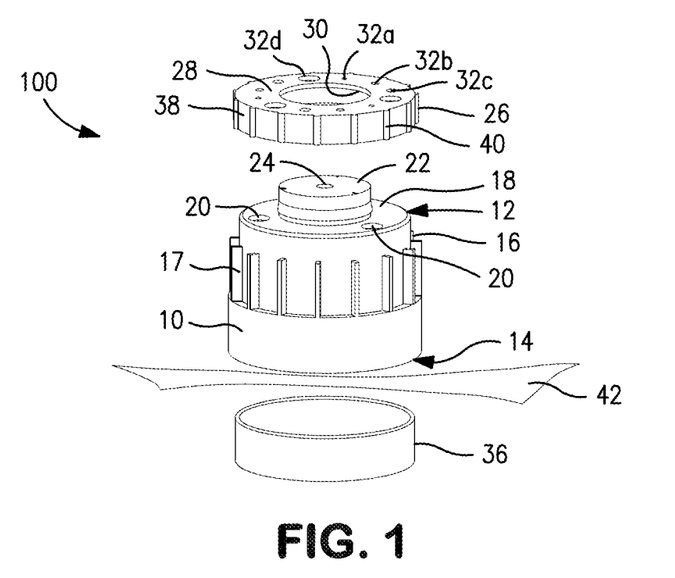
FIG. 1 is an exploded view of the sample cup assembly according to an aspect of the invention.
Figure 2:
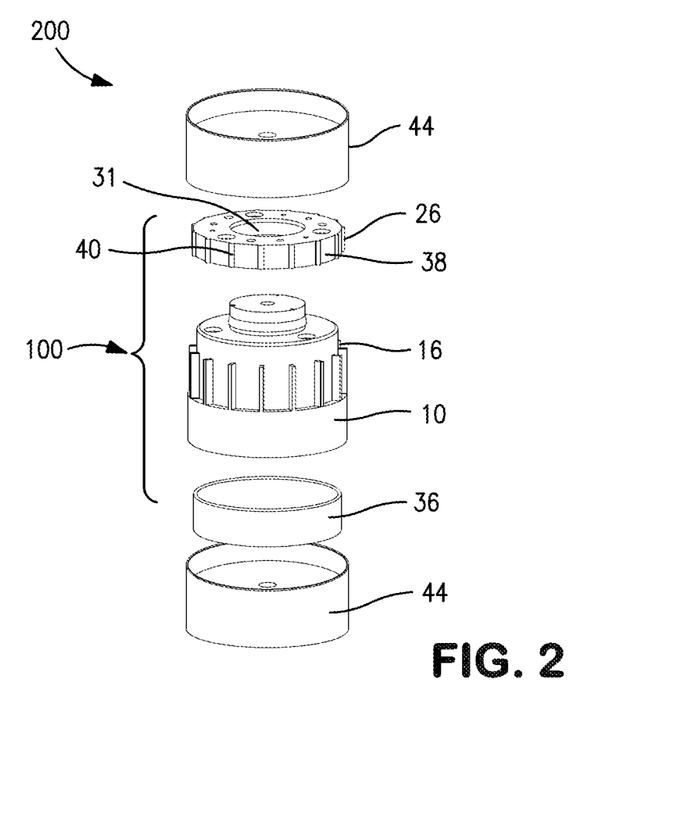
FIG. 2 is an exploded view of the sample cup assembly and system with stacking adapters according to an aspect of the invention.
Figure 4:
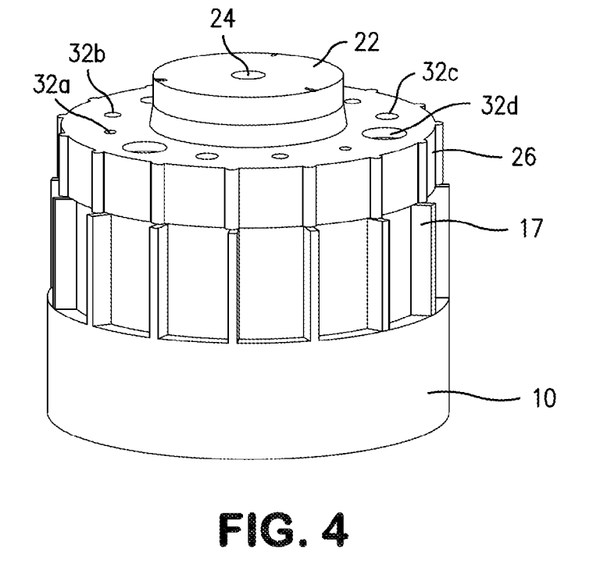
FIG. 4 is a front perspective view illustrating an assembled sample cup according to an aspect of the invention.

Referring to FIGS. 1 and 2, according to an aspect of the invention, a sample cup assembly 100 (FIG. 1) and system 200 (FIG. 2) includes a cell body 10. The cell body 10 includes a partially-closed top end 12, an open-faced bottom end 14, and a substantially cylindrical cell body wall 16 extending axially from the top end 12 to the bottom end 14. Cell body 10 also includes a transverse wall 18 disposed across the top end 12. Transverse wall 18 includes a plurality of apertures 20 disposed about the periphery thereof, which extend from one side of the transverse wall 18 through to the opposite side thereof. Raised portion 22 centrally disposed on the transverse wall 18 includes a central aperture 24 that extends from one side of the raised portion 22 through to the opposite side thereof. The plurality of apertures 20 and the central aperture 24 are in fluid communication with an internal, substantially cylindrical hollow chamber 34 illustrated in FIG. 4. The hollow chamber 34 is defined between the top end 12 and the bottom end 14 of the cell body 10. Chamber 34 is configured for receiving a sample material 48, illustrated in FIG. 12, to be subjected to spectrochemical analysis. In one aspect according to the invention, cell body 10 includes a plurality of ribbed members 17 horizontally disposed about the cell body wall 16 to assist a user in gripping the body 10 upon assembly, or for removal from an analytical instrument.

Still referring to FIGS. 1 and 2, sample cup assembly 100 and system 200 include a rotatable cap 26 that includes a top surface 28, a bottom surface 30, a peripheral side wall 38, a centrally-located aperture 31, and a series of apertures 32a, 32b, 32c and 32d. In one aspect according to the invention, the peripheral sidewall 38 includes a plurality of ribbed members 40 disposed thereon to assist a user in gripping the rotatable cap 26 upon assembly, or for rotation on the cell body 10.

Figure 7:
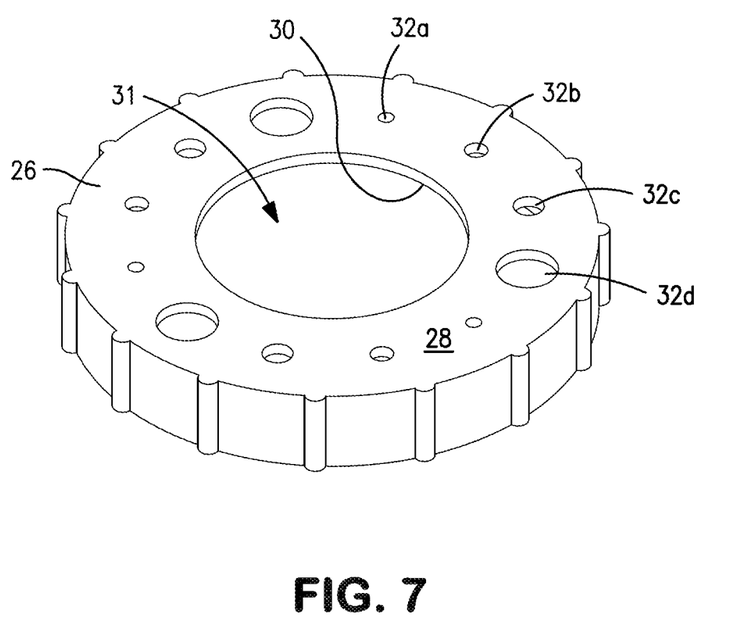
FIG. 7 is a perspective view of a rotatable cap according to an aspect of the invention.

Referring still to FIGS. 1 and 2, each aperture, 32a, 32b, 32c and 32d, has a different diameter. The apertures 32a, 32b, 32c and 32d extend from the top surface 28 through to the bottom surface 30 of the rotatable cap 26. In the cap 26 as illustrated, the repeating series of apertures 32a, 32b, 32c and 32d has four sets of three apertures having an equal diameter, i.e., three 32a apertures, three 32b apertures, three 32c apertures, and three 32d apertures. The series of apertures 32a, 32b, 32c and 32d as illustrated are arranged according to diameter size and increase from smallest to largest, and the pattern is repeated about the periphery of the rotatable cap 26, as also illustrated in FIG. 7. The sequence, or repeating set pattern, of the series of apertures 32a, 32b, 32c and 32d is illustrative only, as it should be understood that any selected pattern may be suitable for use according to an aspect of the invention.

Figure 3:
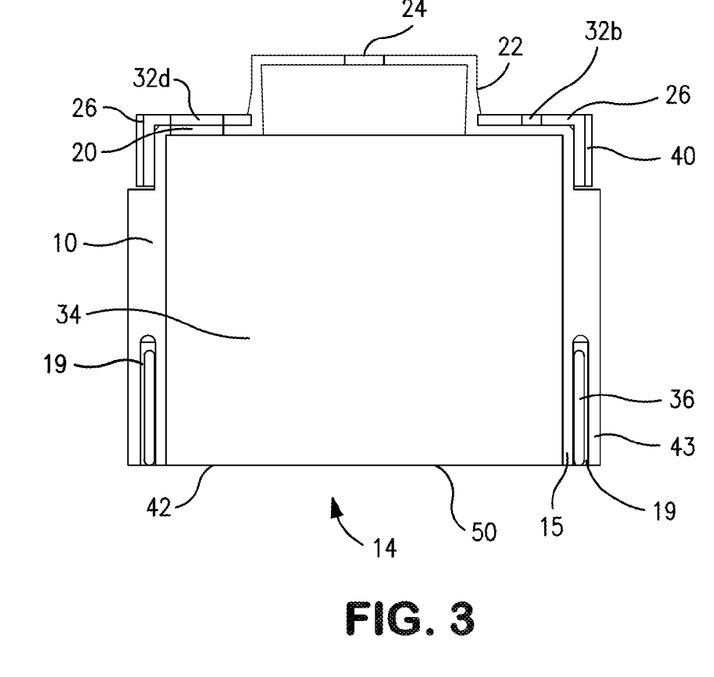
FIG. 3 is a cross-sectional view illustrating an assembled sample cup according to an aspect of the invention.

Referring now to FIG. 3, the open bottom end 14 of cell body 10 includes a peripheral outer wall 13 and peripheral inner wall 15, wherein the space between the peripheral outer wall 13 and peripheral inner wall 15 defines an annular cavity 19 for receiving ring member 36 and a thin film of material 42. Ring member 36 is provided to attach a thin film of material 42 to the open bottom end 14 of cell body 10. Ring member 36 is structured to couple with the bottom end 14 of a cell body 10 by being inserted into the annular cavity 19 to provide a taut sample plane 50 by stretching the thin film of material 42 across the open end 14 thereof upon assembly.

Figure 14:
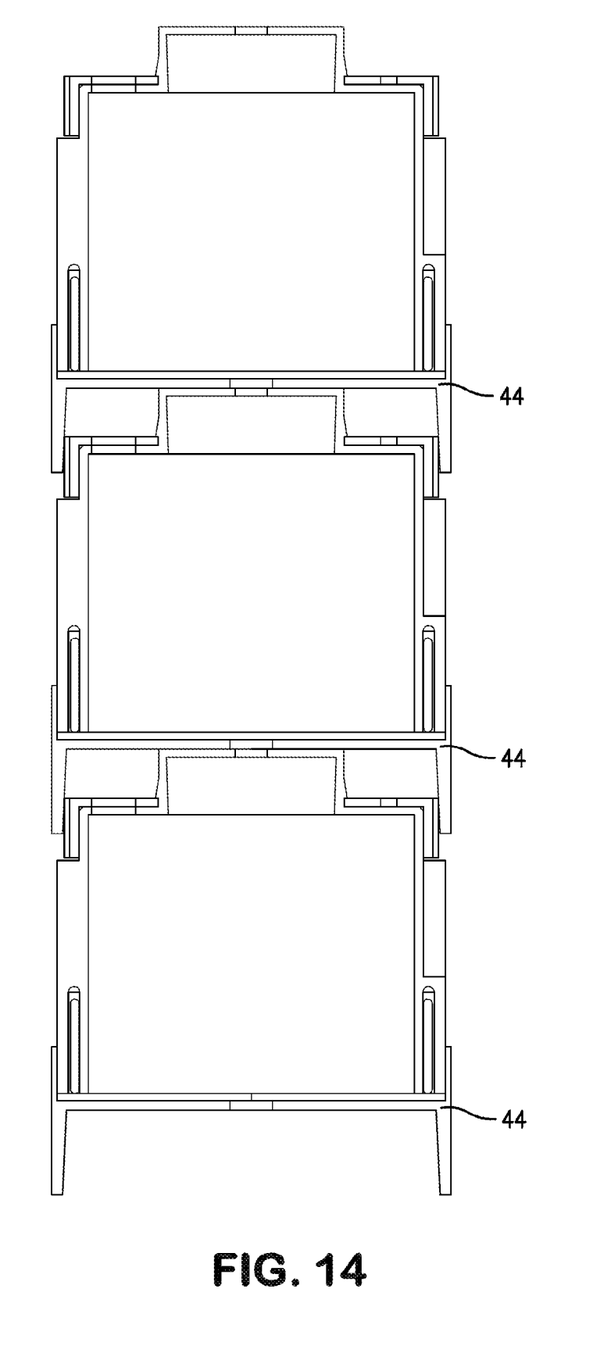
FIG. 14 is a cross-sectional view of a stacked and assembled sample cup system according to an aspect of the invention.

Referring back to FIG. 2, a dual-purpose stacking adapter 44, illustrated in FIG. 2 below ring member 36 at one position, is provided for protecting the taut sample plane 50 during shipping and storage. The dual-purpose stacking adapter 44 is also illustrated at the upper portion of FIG. 2 at another position. Advantageously, as illustrated in FIG. 14, the stacking adapter also provides a user with the ability to stack assembled sample cups (illustrated in FIGS. 3 and 4) for storage or transportation.

Figure 5:
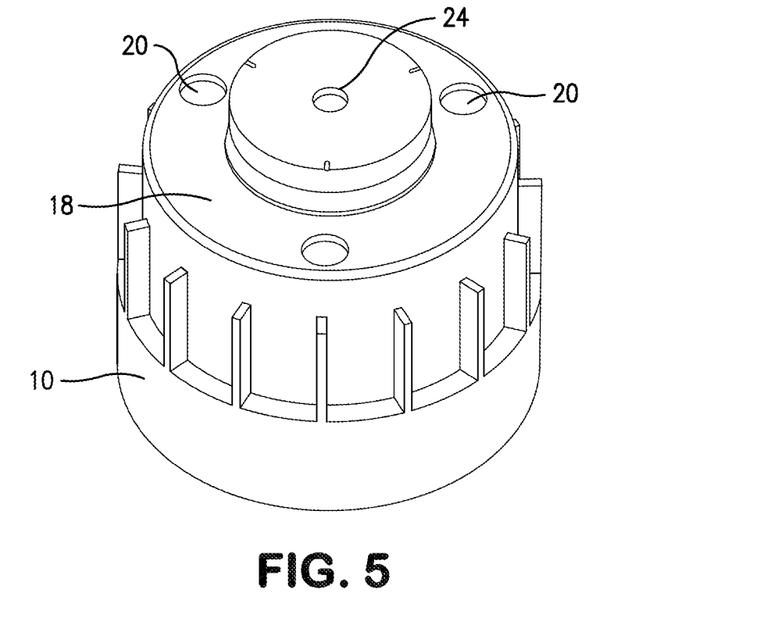
FIG. 5 is a top perspective view illustrating the central aperture and the plurality of apertures of a cell body according to an aspect of the invention.
Figure 6:
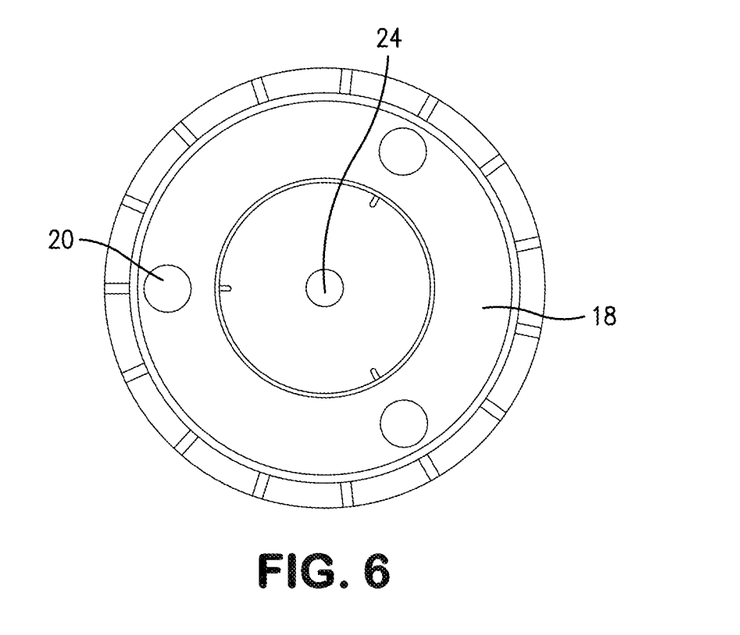
FIG. 6 is a top view of the top end of a cell body illustrating the central aperture and plurality of apertures according to an aspect of the invention.

Referring now to FIGS. 5 and 6, the central aperture 24 of cell body 10 through which gas may be introduced is illustrated. A plurality of apertures 20 on the transverse wall 18 about the periphery thereof are provided through which gas may be vented or evacuated from the hollow chamber 34. Although the plurality of apertures 20 illustrated includes three apertures, there may be more or less apertures present.

Figure 8:
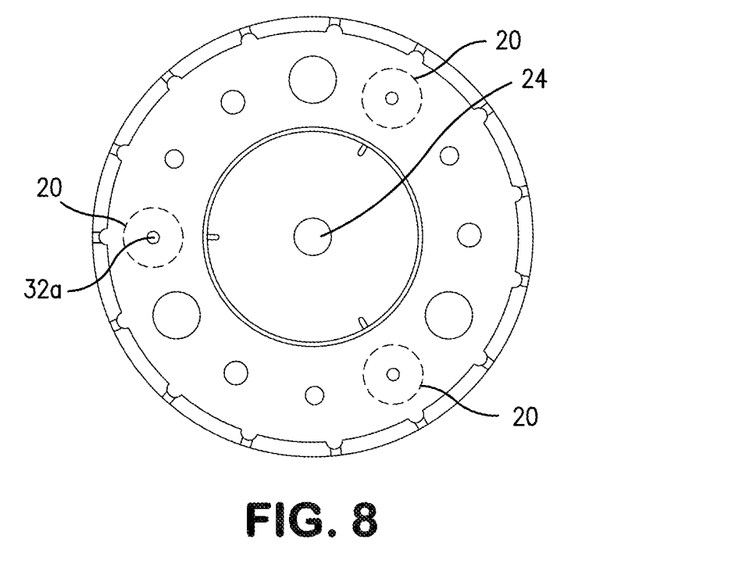
FIG. 8 is a top plan view of the assembly illustrating the selective alignment and position of each of the plurality of apertures on the cell body with one set of the series of apertures on the cap according to an aspect of the invention.
Figure 9:
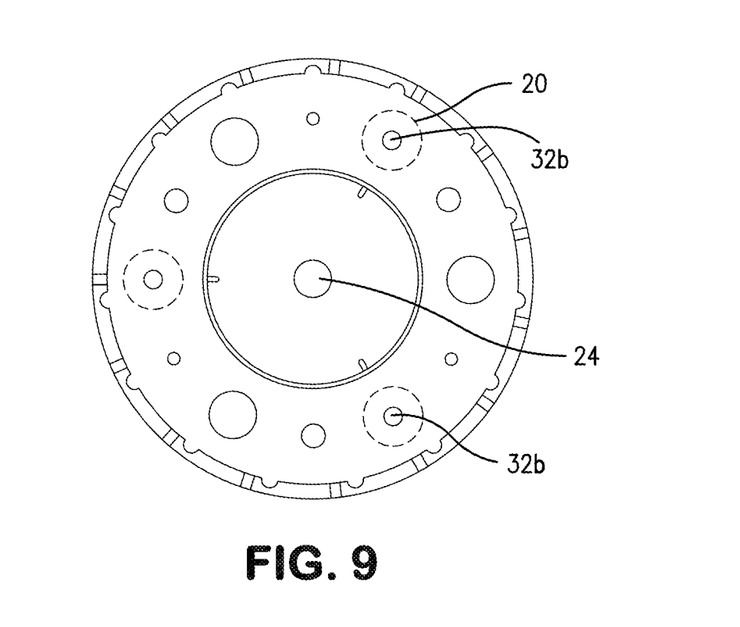
FIG. 9 is a top plan view of the assembly illustrating the selective alignment and position of each of the plurality of apertures on the cell body with another set of the series of apertures on the cap according to an aspect of the invention.
Figure 10:
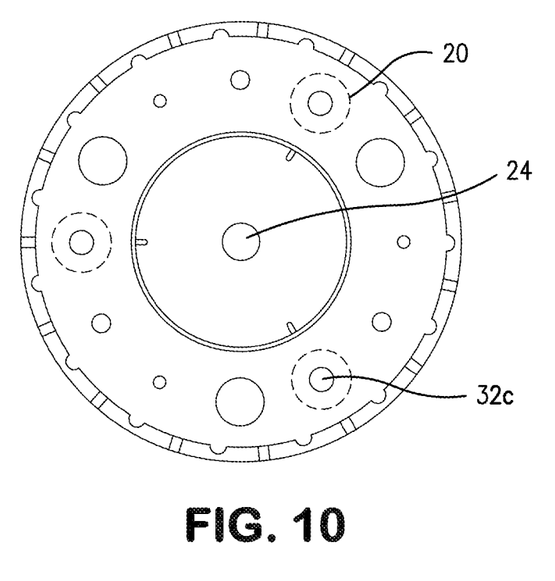
FIG. 10 is a top plan view of the assembly illustrating the selective alignment and position of each of the plurality of apertures on the cell body with yet another set of the series of apertures on the cap according to an aspect of the invention.
Figure 11:
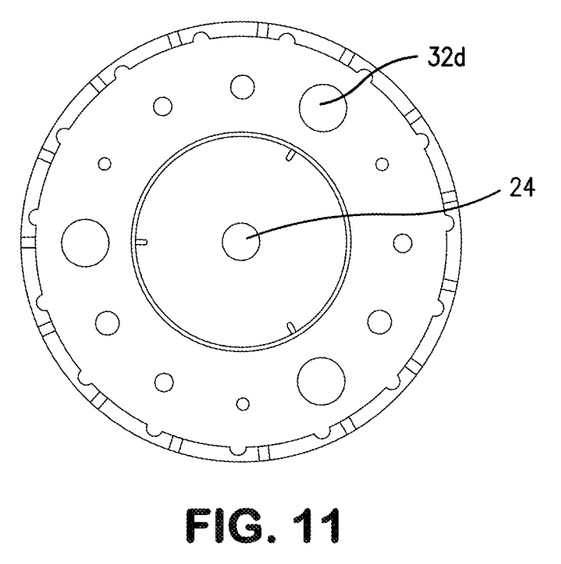
FIG. 11 is a top plan view of the assembly illustrating the selective alignment and position of each of the plurality of apertures on the cell body with yet another set of the series of apertures on the cap according to an aspect of the invention.

Referring now to FIG. 8, each of the plurality of apertures 20 (illustrated in phantom) is aligned with the smallest apertures 32a, at venting position 1. Referring to FIG. 9, the larger apertures 32b are aligned with the plurality of apertures 20, illustrated in phantom, at venting position 2. Referring to FIG. 10, the second-to-largest apertures 32c are aligned with the plurality of apertures 20, illustrated in phantom, at venting position 3. Finally, referring to FIG. 11, the largest apertures 32*d* are aligned with the plurality of apertures 20 at venting position 4. It has been found that in certain instances, particularly involving volatile samples, that when vent holes are too large, a portion of the sample material is evacuated with the gas, which exemplifies the need for the selective alignment of apertures as disclosed herein. Advantageously, one may selectively align each of the plurality of apertures 20 with a corresponding set in the series of apertures 32*a*, 32*b*, 32*c* and 32*d* to control the rate of release of air and gas to reduce or eliminate loss of sample material upon purging with a gas.

Figure 12:
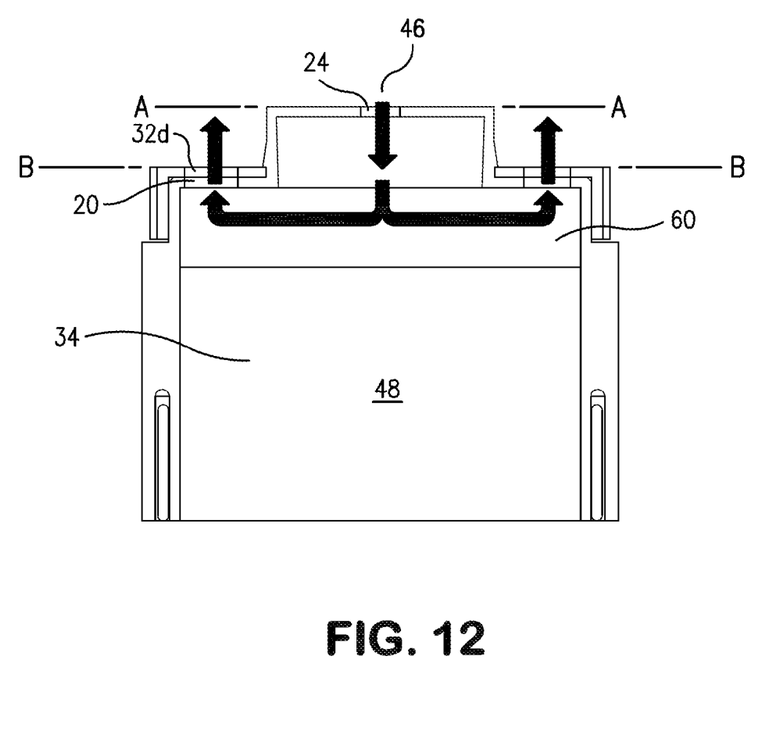
FIG. 12 illustrates the purging process as a gas is introduced through the central aperture of a cell body into a sample chamber, and is vented out through the selectively aligned apertures according to an aspect of the invention.

In instances where the introduction of gas is necessary to remove air from an assembled sample cup 100 to obtain accurate and precise analytical data, an assembled sample cup 100 is placed in a lock-load chamber of an appropriate analytical instrument. An inert purging gas 46, for example, helium or nitrogen, is introduced into the chamber 34 of the cell body 10 through the central aperture 24, as illustrated in FIG. 12. Air purged from the cell body 10 escapes or is vented through the selectively aligned apertures, as illustrated in FIGS. 8-11. Ultimately, the air and inert gas 46 are vented out of the assembled cup 100 and analytical instrument, and the sample cup 100 may be automatically moved from the lock-load position into the analysis chamber of the instrument, and subjected to analysis.

Referring to FIG. 12, the purging process is illustrated as a gas 46 is introduced through the central aperture 24 at upper plane A of the cell body 10 into a hollow sample chamber 34 containing a sample material 48. The gas 46 fills any empty space 60 within the chamber 34 and cup 100, and forces out the air which is vented out at plane B through the selectively aligned apertures (apertures 32*d* are aligned with apertures 20 in this example) according to an aspect of the invention.

Figure 13:
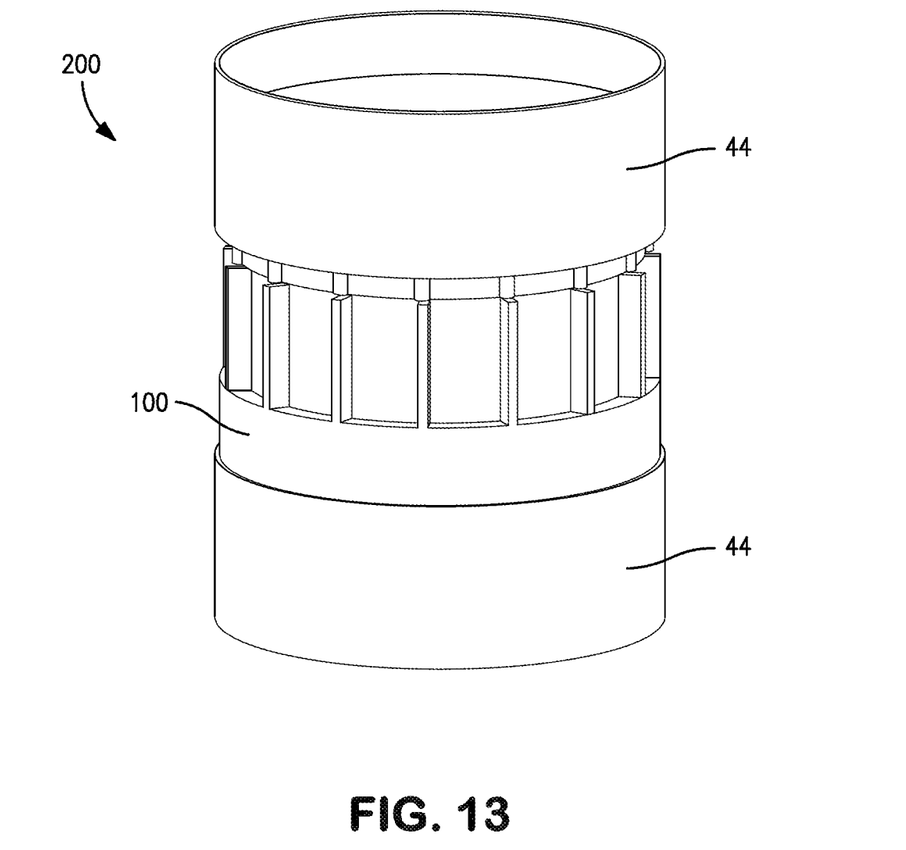
FIG. 13 is an front plan view of an assembled sample cup system including the stacking adapter disposed adjacent the top end and bottom end of an assembled sample cup assembly according to an aspect of the invention.

Referring to FIG. 13, an assembled sample cup system 200 includes a stacking adapter 44 disposed adjacent the top end and bottom end of an assembled sample cup assembly 100 for shipping or storage according to an aspect of the invention.

The method for purging a sample analysis cup according to an aspect of the invention includes the step of providing a cell body 10 including a partially-closed top end 12, an open-faced bottom end 14 and a cell body wall 16 extending axially from the top end 12 to the bottom end 14. Cell body 10 also includes a transverse wall 18 disposed across top end 12. Transverse wall 18 includes a plurality of apertures 20 disposed about the periphery thereof, which extend from one side of the transverse wall 18 through to the opposite side thereof. Raised portion 22 centrally disposed on the transverse wall 18 includes a central aperture 24 that extends from one side of the raised portion 22 through the opposite side thereof. The plurality of apertures 20 and central aperture 24 are in fluid communication with a hollow chamber 34 defined between the top end 12 and the bottom end 14 of the cell body 10. The hollow chamber 34 is configured for receiving a sample material 48 to be subjected to spectrochemical analysis.

The method includes the step of disposing a rotatable cap 26 onto the top end 12 of a cell body 10. The rotatable cap 26 includes a top surface 28, a bottom surface 30, a centrally-located aperture 31, and a series of apertures 32*a*, 32*b*, 32*c* and 32*d* extending from the top surface 28 through to the bottom surface 30 thereof. In the cap 26 illustrated, the series of apertures 32 includes four sets of three apertures having an equal diameter, each set having a different diameter, and arranged according to diameter size. The rotatable cap 26 is structured to engage with the top end 12 of the cell body 10 about the raised portion 24 thereof, and wall 16 and transverse wall 18 of cell body 10.

The method also includes the steps of providing a ring member 36 structured to couple with the bottom end 14 of the cell body 10, and disposing a thin film of material 42 between the bottom end 14 and a ring member 36, and inserting the ring member 36 between peripheral outer wall 13 and peripheral inner wall 15 of cell body 10 into the annular cavity 19, thereby assembling a sample cup 100, rotating the rotatable cap 26 about the top end 12 of the cell body 10 to selectively align the plurality of apertures 20 of the transverse wall 18 with one or more selected apertures from the series of apertures 32*a*, 32*b*, 32*c* and 32*d* of the rotatable cap 26, and introducing a gas 46 through the central aperture 24 to purge the air from the assembled sample cup 100, with the selectively aligned apertures permitting the escape of said gas 46.

Referring to FIG. 14, assembled sample cups 100 are illustrated in a stacked formation which is possible due to the structure of the stacking adapter 44. As can be seen, the sample cups 100 are stacked, one on top of another, with the stacking adapter 44 in two positions. Use of the stacking adapter 44 in one position according to an aspect of the invention helps protect and maintain the taut, flat sample plane 50 of the thin film of material 42 prior to and after analysis. Use of the stacking adapter 44 in another position according to another aspect of the invention also provides protection for the contents during storage or transportation.

The cell body 10, the ring member 36 and rotatable cap 26 may be formed of an appropriate polymer, for example, polyethylene. The thin film of material 42 may be formed from polyethylene, polyester, polyethylene terephthalate, polypropylene, polyimide, polycarbonate, ETNOM, or other materials exhibiting minimal and comparative absorption that are suitable for spectroscopic analysis. The ETNOM brand of thin film material is available from Chemplex Industries, Inc.

The invention has been described with reference to specific embodiments. The benefits, other advantages, and solutions to problems have also been described above with regard to specific embodiments. One of ordinary skill in the art, however, appreciates that various modifications and changes can be made without departing from the scope of the invention as set forth in the claims. Accordingly, the specification is to be regarded in an illustrative manner, rather than with a restrictive view, and all such modifications are intended to be included within the scope of the invention.

What is claimed is:

1. A sample analysis cup assembly, comprising:
   a cell body, comprising:
     a top end;
     a bottom end;
     a cell body wall extending axially from said top end to said bottom end;
     a transverse wall adjacent said top end, including a plurality of apertures extending therethrough;
     a hollow chamber defined between said top end and said bottom end of said cell body; and
     a raised portion on said transverse wall including a central aperture extending therethrough;
   a rotatable cap, comprising:
     a top surface;
     a bottom surface; and
     a series of apertures extending from said top surface through said bottom surface, said rotatable cap being structured to engage with said top end of said cell body and to rotate about the raised portion thereof, said series of apertures being selectively and rotatably alignable with said plurality of apertures of said transverse wall, thereby allowing control of the rate of release of a gas through said selectively aligned apertures upon purging said chamber with a gas through said central aperture; and a ring member structured to couple with said bottom end of said cell body.

2. The sample analysis cup assembly according to claim 1, wherein said series of apertures are arranged in a selected pattern.

3. The sample analysis cup assembly according to claim 2, wherein said apertures have different diameters.

4. The sample analysis cup assembly according to claim 2, wherein the selected pattern is repeated about a periphery of said rotatable cap.

5. The sample analysis cup assembly according to claim 1, wherein said cell body wall includes a plurality of ribbed members.

6. The sample analysis cup assembly according to claim 5, wherein said rotatable cap includes a peripheral sidewall, with a plurality of ribbed members disposed thereon.

7. The sample analysis cup assembly according to claim 1, further comprising:
a thin film of material.

8. The sample analysis cup assembly according to claim 7, wherein said thin film of material comprises a polymer.

9. The sample analysis cup according to claim 8, wherein the polymer is a polyester.

10. A sample cup system, comprising:
a cell body, comprising:
a top end;
a bottom end;
a cell body wall extending axially from said top end to said bottom end;
a transverse wall adjacent said top end, including a plurality of apertures extending therethrough;
a hollow chamber defined between said top end and said bottom end of said cell body; and
a raised portion on said transverse wall including a central aperture extending therethrough;
a rotatable cap, comprising:
a top surface;
a bottom surface; and
a series of apertures extending from said top surface through said bottom surface, said rotatable cap being structured to engage with said top end of said cell body and to rotate about the raised portion thereof, said series of apertures being selectively and rotatably alignable with said plurality of apertures of said transverse wall, thereby allowing control of the rate of release of a gas through said selectively aligned apertures upon purging said chamber with a gas through said central aperture;
a thin film of material;
a ring member structured to couple with said bottom end of said cell body and to attach said thin film of material to said cell body; and
a stacking adapter structured to engage with said rotatable cap and said ring member upon assembly of a sample cup.

11. A method for purging a sample analysis cup, comprising the steps of:
providing a cell body, comprising:
a top end;
a bottom end;
a cell body wall extending axially from said top end to said bottom end;
a transverse wall adjacent said top end, including a plurality of apertures extending therethrough;
a hollow chamber defined between said top end and said bottom end of said cell body; and
a raised portion on said transverse wall including a central aperture extending therethrough;
disposing a rotatable cap onto said cell body, said rotatable cap comprising:
a top surface;
a bottom surface; and
a series of apertures extending from said top surface through said bottom surface, said rotatable cap being structured to engage with said top end of said cell body and to rotate about the raised portion thereof, said series of apertures being selectively and rotatably alignable with said plurality of apertures of said transverse wall, thereby allowing control of the rate of release of a gas through said selectively aligned apertures upon purging said chamber with a gas through said central aperture;
providing a ring member structured to couple with said bottom end of said cell body;
disposing a thin film of material between said bottom end of said cell body and a ring member, thereby assembling a sample cup;
rotating said rotatable cap about said raised portion of said cell body to selectively align said plurality of apertures of said transverse wall with one or more of said selected apertures from said series of apertures; and
introducing a gas into said central aperture to purge said assembled sample cup, said selectively aligned apertures permitting the escape of said gas.

* * * * *